United States Patent
Schönrock et al.

(10) Patent No.: US 6,296,857 B1
(45) Date of Patent: Oct. 2, 2001

(54) COSMETIC OR DERMATOLOGICAL PREPARATIONS COMPRISING OLIGOPEPTIDES FOR LIGHTENING THE SKIN OF AGE MARKS AND/OR FOR PREVENTING TANNING OF THE SKIN, IN PARTICULAR TANNING OF THE SKIN CAUSED BY UV RADIATION

(75) Inventors: Uwe Schönrock, Nahe; Heiner Max, Hamburg, both of (DE); Vincent J. Hearing, Clarksburg, MD (US)

(73) Assignee: Beiersdorf Aktiengesellschaft, Hamburg (DE)

(*) Notice: Subject to any disclaimer, the term of this patent is extended or adjusted under 35 U.S.C. 154(b) by 0 days.

(21) Appl. No.: 09/159,270

(22) Filed: Sep. 23, 1998

(51) Int. Cl.$^7$ ............................................. A61K 7/00
(52) U.S. Cl. ............................ 424/401; 514/17; 514/844
(58) Field of Search ............................ 424/401; 514/17, 514/844

(56) References Cited

FOREIGN PATENT DOCUMENTS

97/00892 * 1/1997 (WO).

* cited by examiner

*Primary Examiner*—Michael A. Williamson
(74) *Attorney, Agent, or Firm*—Norris McLaughlin & Marcus

(57) ABSTRACT

Cosmetic or pharmaceutical preparations which are distinguished by an effective content of one or more monomeric or homo- or heterodimeric or homo- or heterotrimeric or homo- or heterotetrameric oligopeptides, where these oligopeptides are based on a structure Asn-Ser-Leu-Asp-Phe SEQ ID NO: 1 as homo- or heteromonomer.

9 Claims, No Drawings

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 1

Asn Ser Leu Asp Phe
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 2

Asn Ser Leu Asp Phe Ser
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 3

Met Asn Ser Leu Asp Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 4

Met Asn Ser Leu Asp Phe Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 5

Met Asn Ser Leu Asp Phe Ser Ser
 1               5

<210> SEQ ID NO 6
<211> LENGTH: 7
<212> TYPE: PRT
<213> ORGANISM: Artificial Sequence

```
-continued

<220> FEATURE:
<223> OTHER INFORMATION: Description of Artificial Sequence: structural
      base for oligopeptides

<400> SEQUENCE: 6

Ser Met Asn Ser Leu Asp Phe
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 7

Ser Met Asn Ser Leu Asp Phe Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: structural
      base for oligopeptides

<400> SEQUENCE: 8

Ser Met Asn Ser Leu Asp Phe Ser Ser
 1               5
```

COSMETIC OR DERMATOLOGICAL PREPARATIONS COMPRISING OLIGOPEPTIDES FOR LIGHTENING THE SKIN OF AGE MARKS AND/OR FOR PREVENTING TANNING OF THE SKIN, IN PARTICULAR TANNING OF THE SKIN CAUSED BY UV RADIATION

The present invention relates to cosmetic or dermatological preparations comprising oligopeptides, for using active ingredients known per se, for cosmetic and topical dermatological lightening of the skin or for preventing tanning of the skin, in particular tanning of the skin caused by UV radiation.

In a preferred embodiment, the present invention relates to cosmetic and dermatological preparations for the prophylaxis and treatment of cosmetic or dermatological changes in the skin such as, for example, undesired pigmentation, for example local hyperpigmentations and malpigmentations (for example lentigo, freckles), but also for the purely cosmetic lightening of large areas of skin whose pigmentation is quite adequate for the individual skin type.

The factors which are responsible for skin pigmentation are the melanocytes which are found in the lowest layer of the epidermis, the stratum basale, next to the basal cells, as pigment-forming cells which occur either singly or more or less in clusters, depending on the skin type. Melanocytes contain melanosomes as characteristic cell organelles, and these form melanin at higher rates when stimulated by UV radiation. The melanin is transported into the keratinocytes and leads to a more or less pronounced tan or brown skin colour.

Melanin is the end product of an oxidative process in which tyrosine is converted with the aid of the enzyme tyrosinase via 3,4-dihydroxyphenylalanine (dopa), dopaquinone, leucodopachrome, dopachrome, 5,6-dihydroxyindole and indole-5,6-quinone to give, finally, melanin.

Hyperpigmentation problems of the skin have a multiplicity of causes and/or accompanying symptoms of a large number of biological processes, for example UV radiation (for example, freckles, ephelides), genetic predisposition, malpigmentation of the skin in the course of wound healing and/or wound scarring or skin ageing (for example *lentigines seniles*).

Active ingredients and preparations which counteract skin pigmentation are known. Products which are essentially used in practice are based on hydroquinone but, on the one hand, only become effective after several weeks' use and, on the other hand, unduly long use of such products is unacceptable for toxicological reasons. Inhibition of tyrosinase by substances such as kojic acid, ascorbic acid and azelaic acid and their derivatives is also well known, but has cosmetic and dermatological disadvantages.

It was an object of the present invention to remedy these shortcomings.

The publication WO-97/00892 describes the depigmenting action of the signal proteins of agoutis (rodent family of the Dasyproctidae, occurrence: approx. 20 species in the woodlands of Central America).

Surprisingly, the object is achieved by cosmetic or pharmaceutical preparations which are distinguished by an effective content of one or more monomeric or homo- or heterodimeric or homo- or heterotrimeric or homo- or heterotetrameric oligopeptides, (1) where these oligopeptides are based on a structure Asn-Ser-Leu-Asp-Phe (or NSLDF) SEQ ID NO: 1 as homo- or heteromonomer, (2) where structures as mentioned above are present in the monomeric or homo- or heterodimeric or homo- or heterotrimeric or homo- or heterotetrameric oligopeptides, with the difference that the C-terminus and/or the N-terminus is complemented by up to 5 amino acids, as shown by the structure

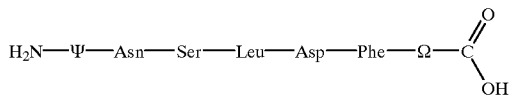

where Ψ and Ω independently of one another may represent amino acid sequences of 0 up to 5 amino acids, (3) or where amino acid sequences shown under items (1) and (2) occur as single or repetitive structural motifs in monomeric or homo-/hetero-di-, -tri- or -tetrameric oligopeptides or proteins with a molecular weight of between approx. 0.5 and 100 kdalton, (4) or where the monomeric or homo-/hetero-di-, -tri, or -tetrameric oligopeptides or proteins are acylated on the C-terminus, as shown by the structure

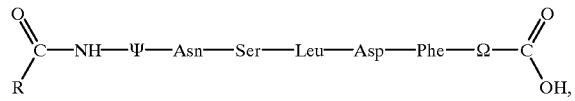

where Ψ and Ω independently of one another may represent amino acid sequences of 0 up to 5 amino acids and R represents a branched or unbranched, saturated or unsaturated hydrocarbon radical, in particular an alkyl radical having 1 to 30 carbon atoms, (5) or where the monomeric or homo-/hetero-di-, -tri-, or -tetrameric oligopeptides or proteins are amidated on the C-terminus, as shown by the structure

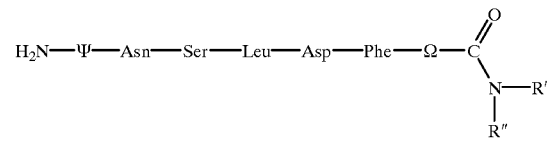

where Ψ and Ω independently of one another may represent amino acid sequences of 0 up to 5 amino acids and where R' and R" independently of one another may be selected from the group consisting of hydrogen and the branched or unbranched, saturated or unsaturated hydrocarbon radicals, in particular the alkyl radical having 1 to 30 carbon atoms, (6) or where the monomeric or homo-/hetero-di-, -tri-, or -tetrameric oligopeptides or proteins are amidated on the C-terminus and acylated on the N-terminus, as shown by the structure

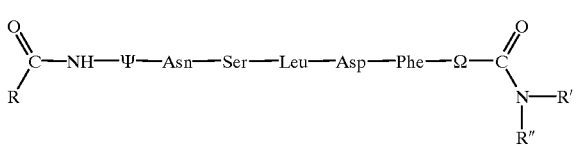

where Ψ and Ω independently of one another may represent amino acid sequences of 0 up to 5 amino acids, R represents a branched or unbranched saturated or unsaturated hydrocarbon radical, in particular an alkyl radical having 1 to 30 carbon atoms, and where R' and R" independently of one another may be selected from the group consisting of hydrogen and the branched or unbranched, saturated or unsaturated hydrocarbon radicals, in particular the alkyl radical having 1 to 30 carbon atoms, (7) or where amino acid sequences occur in monomeric or homo-/hetero-di-, -tri- or -tetrameric oligopeptides or proteins as single or repetitive structural motifs, as shown by the structures

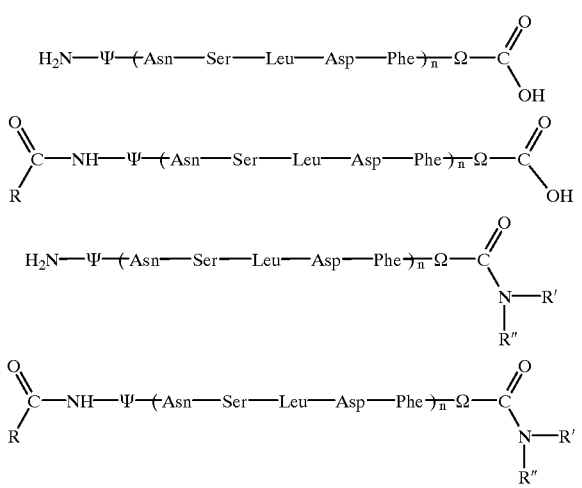

where Ψ may represent a single bond or an amino acid sequence of up to 5 amino acids, Ω may represent an amino acid sequence of up to 15 amino acids, n represents a number from 1 to 25, R represents a branched or unbranched saturated or unsaturated hydrocarbon radical, in particular an alkyl radical of 1 to 30 carbon atoms, and where R' and R" independently of one another may be selected from the group consisting of hydrogen and the branched or unbranched, saturated or unsaturated hydrocarbon radicals, in particular the alkyl radical having 1 to 30 carbon atoms.

Also considered to be an advantageous embodiment of the present invention is the use of one or more monomeric or homo- or heterodimeric or homo- or heterotrimeric or homo- or heterotetrameric oligopeptides, (1) where these oligopeptides are based on a structure Asn-Ser-Leu-Asp-Phe (or NSLDF) SEQ ID NO: 1 as homo- or heteromonomer, (2) where, in the sequence Asn-Ser-Leu-Asp-Phe, in each case one valine may be replaced by an amino acid selected from the group consisting of glycine, alanine, leucine, isoleucine, serine, threonine and methionine, preferably alanine, while the remainder of the sequence is retained, (3) or where structures as mentioned above are present in the monomeric or homo- or heterodimeric or homo- or heterotrimeric or homo- or heterotetrameric oligopeptides, with the difference that the C-terminus and/or the N-terminus is complemented by up to 5 amino acids, as shown by the structure

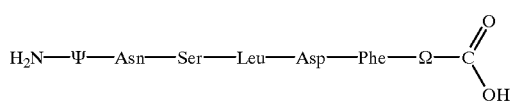

where Ψ and Ω independently of one another may represent amino acid sequences of 0 up to 5 amino acids, (4) or where amino acid sequences shown under items (1) and (2) occur as single or repetitive structural motifs in monomeric or homo-/hetero-di-, tri- or -tetrameric oligopeptides or proteins with a molecular weight of between approx. 0.5 and 100 kdalton, (5) or where the monomeric or homo-/hetero-di-, Tri-, or -tetrameric oligopeptides or proteins are acylated on the N-terminus, as shown by the structure

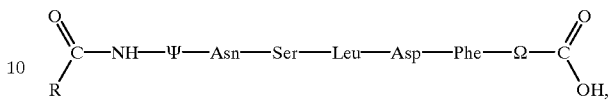

where Ψ and Ω independently of one another may represent amino acid sequences of 0 up to 5 amino acids and R represents a branched or unbranched saturated or unsaturated hydrocarbon radical, in particular an alkyl radical having 1 to 30 carbon atoms, (6) or where the monomeric or homo-/hetero-di-, tri-, or -tetrameric oligopeptides or proteins are amidated on the C-terminus, as shown by the structure

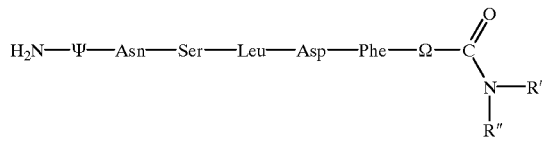

where Ψ and Ω independently of one another may represent amino acid sequences of 0 up to 5 amino acids and R represents a branched or unbranched saturated or unsaturated hydrocarbon radical, in particular an alkyl radical having 1 to 30 carbon atoms, (6) or where the monomeric or homo-/hetero-di-, tri-, or -tetrameric oligopeptides or proteins are amidated on the C-terminus, as shown by the structure

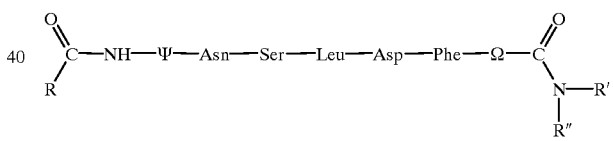

where Ψ and Ω independently of one another may represent amino acid sequences of 0 up to 5 amino acids, R represents a branched or unbranched saturated or unsaturated hydrocarbon radical, in particular an alkyl radical having 1 to 30 carbon atoms, and where R' and R" independently of one another may be selected from the group consisting of hydrogen and the branched or unbranched, saturated or unsaturated hydrocarbon radicals, in particular the alkyl radical having 1 to 30 carbon atoms, (7) or where amino acid sequences occur in monomeric or homo-/hetero-di-, -tri- or -tetrameric oligopeptides or proteins as single or repetitive structural motifs, as shown by the structures

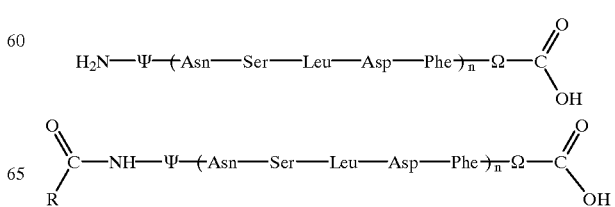

-continued

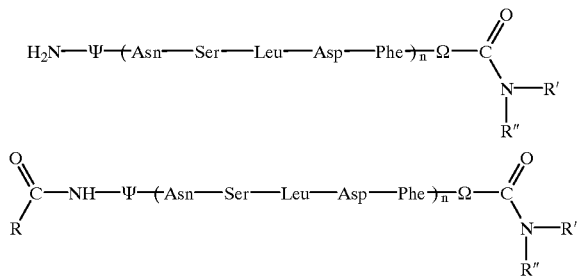

where Ψ may represent a single bond or an amino acid sequence of up to 5 amino acids, Ω may represent an amino acid sequence of up to 15 amino acids, n represents a number from 1 to 25, R represents a branched or unbranched saturated or unsaturated hydrocarbon radical, in particular an alkyl radical of 1 to 30 carbon atoms, and where R' and R" independently of one another may be selected from the group consisting of hydrogen and the branched or unbranched, saturated or unsaturated hydrocarbon radicals, in particular the alkyl radical having 1 to 30 carbon atoms.

The amino acid sequences which optionally complement the peptide sequence on the C- or N-terminus are preferably constituted of proteinogenic amino acids.

The proteinogenic amino acids and their corresponding three- and single-letter codes are shown in Table 1.
Table: Three- and single-letter codes for amino acids

| Amino acid | | |
|---|---|---|
| L-alanine | Ala | A |
| L-valine | Val | V |
| L-leucine | Leu | L |
| L-isoleucine | Ile | I |
| L-proline | Pro | P |
| L-tryptophan | Typ | |
| L-phenylalanine | Phe | F |
| L-methionine | Met | M |
| glycine | Gly | G |
| L-serine | Ser | S |
| L-tyrosine | Tyr | Y |
| L-threonine | Thr | T |
| L-cysteine | Cys | C |
| L-asparagine | Asn | N |
| L-glutamine | Gln | Q |
| L-aspartic acid | Asp | D |
| L-glutamic acid | Glu | E |
| L-lysine | Lys | K |
| L-arginine | Arg | R |
| L-histidine | His | H |

L-Selenocysteine may replace L-cysteine, and L-selenomethionine L-methionine. In addition, individual, several or else all positions may also be replaced by the corresponding stereoisomers in the D-configuration.

Examples of especially advantageous oligopeptides according to the invention are Asn-Ser-Leu-Asp-Phe, SEQ ID NO: 1 Asn-Ser-Leu-Asp-Phe-Ser, SEQ ID NO: 2 Met-Asn-Ser-Leu-Asp-Phe, SEQ ID NO: 3 Met-Asn-Ser-Leu-Asp-Phe-Ser, SEQ ID NO: 4 Met-Asn-Ser-Leu-Asp-Phe-Ser-Ser, SEQ ID NO: 5 Ser-Met-Asn-Ser-Leu-Asp-Phe, SEQ ID NO: 6 Ser-Met-Asn-Ser-Leu-Asp-Phe-Ser SEQ ID NO: 7 as well as Ser-Met-Asn-Ser-Leu-Asp-Phe-Ser-Ser, SEQ ID NO: 8.

Preferred acylated oligopeptides are those which are acylated on the N-terminus with unbranched alkanoyl groups.

It may be preferable to synthesize the peptides of the present invention using recombinant DNA methods. Alternatively, it may be preferable to synthesize the peptides of the present invention using the well-known chain elongation techniques such as solid-phase synthesis, as on a Merrifield resin or the like.

To synthesize a peptide using recombinant DNA, one typically synthesizes a double-stranded DNA chain which encodes the desired amino acid sequence. The degeneracy of the genetic code permits a wide variety of codon combinations to be used to form the DNA chain that encodes the product peptide. Certain particular codons are more efficient for peptide expression in certain types of organisms and the selection of codons preferably is made according to those codons which are most efficient for expression in the type of organism which is to serve as the host for the recombinant vector. However, any correct set of codons should encode the desired product, even if slightly less efficiently. Codon selection may also depend upon vector construction considerations, for example, it may be necessary to avoid creating a particular restriction site in the DNA chain if, subsequent to insertion of the synthetic DNA chain, the vector is to be manipulated using a restriction enzyme that cleaves at such a site. Also, it is necessary to avoid placing restriction sites in the DNA chain if the host organism which is to be transformed with the recombinant vector containing the DNA chain is known to produce a restriction enzyme that would cleave at such a site within the DNA chain.

In addition to the encoding sequences, the DNA chain that is synthesized may contain additional sequences, depending upon vector construction considerations. Typically, a DNA chain is synthesized with linkers at its ends to facilitate insertion into restriction sites within a cloning vector. The DNA chain may be constructed so as to encode the desired sequence as a portion of a fusion peptide and if so, it may contain terminal sequences that encode amino acid residue sequences that serve as proteolytic processing sites, whereby the desired peptide may be proteolytically cleaved from the remainder of the fusion peptide. The terminal portions of the synthetic DNA chain may also contain appropriate start and stop signals.

To assemble the desired DNA chain, oligonucleotides are constructed by conventional methods such as procedures described in T. Maniatis et al. COLD SPRING HARBOR LABORATORY MANUAL, Cold Spring Harbor, N.Y. (1982) (hereinafter CSH). Sense and antisense oligonucleotide chains up to about 70 nucleotide residues long are synthesized preferably on automated synthesizers such as the Applied Biosystems in model 380B DNA synthesizer. The oligonucleotide chains are constructed so that the sense and antisense oligonucleotides associate with each other through hydrogen bonding between complementary base pairs and thereby form double-stranded chains. These oligonucleotides are then ligated to the vector.

The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as E. coli, the DNA chain will be inserted 3' of a promoter sequence, a Shine-Delgamo sequence (or ribosome binding site) that is within a 5' non-translated portion and an ATG start codon. The ATG start codon is appropriately spaced from the Shine-Delargo sequence, and the encoding sequence is placed in correct reading frame with the ATG start codon. The cloning vector also provides a 3' non-translated region and a transcription termination site. A translation termination site could be provided by either the synthetic DNA or the cloning vector. For insertion into a eukaryotic cell, such as a yeast cell or a cell line obtained from a higher animal, the encoding oligonucleotide sequence is appropriately spaced from a capping site and in correct reading frame with an ATG start signal. The cloning vector also provides a 3' non-translated region and a poly-adenylation site. A translation termination site could be provided by either the synthetic DNA or the vector.

Derivatives of prokaryotic vectors, such as pBR322, pMB9, Col El, pCRI, RP4 and lambda-phage, are available for inserting a DNA chain of the length necessary to encode peptides of interest with substantial assurance of at least some expression of the encoded peptide. Typically, such vectors are constructed or modified to have a unique restriction site(s) appropriately positioned relative to a promoter, such as the lac promoter. The DNA chain may be inserted with appropriate linkers into such a restriction site, with substantial assurance of production of peptide in a prokaryotic cell line transformed with the recombinant vector. To assure the proper reading frame, linkers of various lengths may be provided at the ends of the peptide-encoding sequence. Cassettes, which include sequences, such as the 5' region of the lac Z gene (including the operator, promoter, transcription start site, Shine Delgamo sequence and translation initiation signal), the regulatory region from the tryptophan gene (trp operator, promoter, ribosome binding site and translation initiator) and a fusion gene containing these two promoters, called the trp-lac or commonly called the Tac promoter, are available into which a synthetic DNA chain may be conveniently inserted.

Similarly, eukaryotic transformation vectors, such as the cloned bovine papilloma virus genome, the cloned genomes of the murine retroviruses, and eukaryotic cassettes, such as the pSV-2 gpt system (described by Mulligan and Berg, NATURE, Vol. 277, pp. 108–114,1979), the Okayama-Berg cloning system (MOL. CELL BIOL., Vol. 2, pp. 161–170, 1982) and the expression cloning vector recently described by Genetics Institute (SCIENCE, Vol. 228, pp. 810–815, 1985). These provide substantial assurance of at least some expression of the peptide in the transformed eukaryotic cell line.

Another way to produce desired peptides is to produce the peptide initially as a segment of a gene-encoded fusion peptide. In such a case, the DNA chain is constructed so that the expressed peptide has enzymatic processing sites flanking the peptide sequence or, more commonly, processing site at one side of the desired peptide. A peptide-encoding DNA chain may be inserted for example, into the beta-galactosidase gene for insertion into *E. coli*, in which case, the expressed fusion peptide is subsequently cleaved with appropriate proteolytic enzymes to release the peptide from beta-galactosidase peptide sequences.

Alternatively, the peptides can be synthesized by suitable chain elongation or coupling-type methods, such as by exclusively solid-phase techniques, by partial solid-phase techniques, by fragment condensation or by classical solution couplings. The techniques of exclusively solid-phase synthesis are set forth in the textbook "Solid-Phase Peptide Synthesis" Stewart & Young, Pierce Chemical Company, Rockford, Ill., 1984 and are exemplified by the disclosure of U.S. Pat. No. 4,105,603, issued Aug. 8, 1978, incorporated herein by reference. The fragment condensation method of synthesis is exemplified in U.S. Pat. No. 3,972,859 issued Aug. 3, 1976, incorporated herein by reference. Other available syntheses are exemplified by U.S. Pat. No. 3,842,067, issued Oct. 15, 1974 and U.S. Pat. No. 3,862,925 issued Jan. 28, 1975, both incorporated herein by reference.

Common to coupling-type syntheses is the protection of the labile side chain groups of the various amino acid moieties with suitable protecting groups which will prevent a chemical reaction from occurring at that site until the group is ultimately removed. Usually also common is the protection of an alpha-amino group by an amino-terminus blocking group on an amino acid or a fragment while that entity reacts at the carboxyl group, followed by the selective removal of the amino-terminus blocking group to allow subsequent reaction to take place at that location. Accordingly, it is common that, as a step in the synthesis, an intermediate compound is produced which includes each of the amino acid residues located in its desired sequence in the peptide chain with side-chain protecting groups or terminus blocking group linked to the appropriate residues.

In selecting a particular side chain protecting group to be used in the synthesis of the peptides, the following rules are followed: (a) the protecting group should be stable to the reagent and under the reaction conditions selected for removing the .alpha.-amino protecting group at each step of the synthesis, (b) the protecting group should retain its protecting properties and not be split off under coupling conditions, and (c) the side chain protecting group should be removable, upon the completion of the synthesis containing the desired amino acid sequence, under reaction conditions that will not after the peptide chain.

The peptides are preferably prepared using solid phase synthesis, such as that described by Merrifield, J. AM. CHEM. SOC., Vol. 85, pp. 2149 (1963), although other equivalent chemical syntheses known in the art can also be used as previously mentioned. Solid-phase synthesis is commenced from the C-terminal end of the peptide by coupling a protected a-amino acid to a suitable resin. Such a starting material can be prepared by attaching a-amino-protected Val by an ester linkage to a chloromethylated resin or a hydroxymethyl resin, or by an amide bond to a butylated hydroxy anisole (BHA) resin or MBHA resin. The preparation of the hydroxymethyl resin is described by Bodansky et al., CHEM. IND. (London) Vol. 38, pp. 1597–98 (1966). Chloromethylated resins are commercially available from Bio Rad Laboratories, Richmond, Calif. and from Lab. Systems, Inc. The preparation of such a resin is described by Stewart et al, "Solid Phase Peptide Synthesis" (Freeman & Co., San Francisco 1969), Chapter 1, pp. 1–6. BHA and MBHA resin supports are commercially available and are generally used only when the desired polypeptide being synthesized has an a-carboxamide at the C-terminal.

Activating reagents used in solid phase synthesis of the peptides are well known in the peptide synthesis art. Examples of suitable activating reagents are (1) carbodiimides, such as N,N-diisopropylcarbodiimide, N,N-dicyclohexylcarbodiimide (DCCI); (2) cyanamides such as N,N-dibenzylcyanamide; (3) keteimines; (4) isoxazolium salts, such as N-ethyl-5-phenyl isoxazolium-3-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N-carbonyl diimidazole, N,N-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) reagents which form an active ester with the carboxyl moiety of the amino acid, such as nitrogen-containing heterocyclic compounds having a hydroxy group on one ring nitrogen, e.g. N-hydroxyphthalimide, N-hydroxysuccinimide and 1-hydroxybenzotriazole (HOBT). Other activating reagents and their use in peptide coupling are described by Schroder & Lubke supra, in Chapter III and by Kapoor, J. PHAR. SCI., Vol. 59, pp. 1–27 (1970).

Each protected amino acid or amino acid sequence is introduced into the solid phase reactor in about a two-fold or more excess, and the coupling may be carried out in a medium of dimethylformamide (DMF)—$CH_2 C_{12}$ (1:1) or in DMF or $CH_2Cl_6$ alone. In cases where incomplete coupling occurs, the coupling procedure is repeated before removal of the a-amino protecting group prior to the coupling of the next amino acid. If performed manually, the success of the coupling reaction at each stage of the synthesis is monitored by the ninhydrin reaction, as described by E. Kaiser et al., ANAL. BIOCHEM., Vol. 34, pp. 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$, $X^8$ and $X^9$ and the a-amino protecting group $X^1$ to obtain the peptide.

As an alternative route, the intermediate peptide may be separated from the resin support by alcoholysis after which the recovered C-terminal alkyl ester is converted to the acid by hydrolysis. Any side chain protecting groups may then be cleaved as previously described or by other known procedures, such as catalytic reduction (e.g. Pd on $BaSO_4$). When using hydrogen fluoride for cleaving, anisole and methylethyl sulphide are included in the reaction vessel for scavenging.

For example, single peptides can be prepared advantageously with the aid of an automatic MilliGen 9050 peptide synthesizer, overlapping peptides with the aid of a multiple peptide synthesizer SMPS 350 (ZINSSER Analytik) by means of solid-phase synthesis (R. B. Merrifield (1966) J. Am. Chem. Soc. 85, 2149) following the Fmoc/But strategy (E. Atherton, R. C. Sheppard; "Solid-Phase Peptide Synthesis: A Practical Approach", IRL Press, Oxford, England (1989).

Coupling and cleavage steps may be checked by means of on-line UV monitoring. A substance which can advantageously be used as solid-phase matrix for free peptides is, for example, a p-alkoxybenzyl alcohol-modified polystyrene resin (S.-S. Wang; J. Am. Chem. Soc. 95 (1973), p. 1328), as solid-phase matrix for peptide amides Rink amide resin (H.Rink; Tetrahedron Left. 28 (1987), p. 3787). TBTU (2-(1H-benzotriazol-1-yl)-1,1,3,3-tetramethyluronium tetrafluoroborate) may advantageously be employed as coupling reagent (R. Knorr, A. Trzeciak, W. Bannwarth, D. Gillesen; Tetrahedron Lett. 30 (1989), p. 1927). Usual coupling times are in each 10–30, in particular approx. 20, minutes. After the synthesis has ended, the peptides may be cleaved from the resin, for example with the aid of trifluoroacetic acid and, if desired, added substances (for example phenol, thioanisole, but also water) and simultaneously freed from all protective groups.

The reaction solution may give a crude product, for example by dropwise addition to ice-cold diethyl ether, which can be purified, if desired, by washing with a suitable washing fluid, for example cold diethyl ether, and then lyophilized. The crude peptide is then subjected to ultrapurification to a purity of >98%, advantageously by means of preparative reversed-phase high-performance liquid chromatography (RP-HPLC) on a C18-column (250×10 mm) using an acetonitrile/0.05% trifluoroacetic acid/water system.

Peptides which are acylated by the N-terminus can be obtained in high yields by reacting the N-terminally deprotected peptides which are bound to the resin with acid chlorides or acid anhydrides (for example palmitoyl chloride or lauryl chloride) in a suitable solvent (for example dimethylformamide/N-methylmorpholine).

The cosmetically or pharmaceutically acceptable oligopeptides used in accordance with the invention, hereinbelow also collectively termed "active ingredient used in accordance with the invention", irrespective of whether an individual substance or an isomer mixture or a mixture of a variety of individual substances is present, have shown to be outstanding active ingredients against undesired pigmentation, in particular local hyperpigmentation, both preventatively and therapeutically.

The content of active ingredient used in accordance with the invention in the cosmetic or topical dermatological preparations may, in accordance with the invention, amount to 0.000001–10% by weight, preferably 0.00001–1% by weight, in particular 0.0001–0.1% by weight, based on the total weight of the preparations.

Surprisingly, it has emerged that the objects on which the invention is based are achieved by the active ingredient used in accordance with the invention. When using the active ingredient used in accordance with the invention, or cosmetic or topical dermatological preparations with an effective content of active ingredient used in accordance with the invention, effective prophylaxis against undesired pigmentation is possible. According to the invention, it is, in particular, extremely advantageous to use the active ingredient used in accordance with the invention, or cosmetic or topical dermatological preparations with an effective content of active ingredient used in accordance with the invention, for the cosmetic or dermatological treatment of undesired skin pigmentation, that is, for example, *Lentigines seniles.*

The prophylaxis and/or the cosmetic or dermatological treatment with the active ingredient used in accordance with the invention, or with the cosmetic or topical dermatological preparations with an effective content of active ingredient used in accordance with the invention, is effected in the customary manner by applying the active ingredient used in accordance with the invention, or the cosmetic or topical dermatological preparations with an effective content of active ingredient used in accordance with the invention, to the affected parts of the skin.

The active ingredient used in accordance with the invention may advantageously be incorporated into customary cosmetic and dermatological preparations, which may exist in a variety of forms. For example, they may be a solution, a water-in-oil (W/O) type emulsion, an oil-in-water (O/W) type emulsion, or a multiple emulsion, for example a water-in-oil-in-water (W/O/W) or oil-in-water-in-oil (O/W/O) emulsion, a hydrodispersion or lipodispersion, a gel, a solid stick or else an aerosol.

Emulsions in accordance with the present invention, for example in the form of a cream, a lotion or a cosmetic milk, are advantageous and comprise, for example, fats, oils, waxes and/or other lipids, as well as water and one or more emulsifiers as they are usually used for such a type of formulation.

It is also possible and advantageous in accordance with the present invention to incorporate the active ingredient used in accordance with the invention into aqueous systems or surfactant preparations for cleansing skin and hair.

Naturally, the expert knows that high-quality cosmetic compositions are unthinkable without the customary adjuvants and additives in most cases. These include, for example, thickeners, fillers, fragrance, colours, emulsifiers, additional active ingredients such as vitamins or proteins, sunscreens, stabilizers, insect repellants, alcohol, water, salts, antimicrobially, proteolytically or keratolytically active substances, and the like.

The same also applies analogously to corresponding requirements regarding the formulation of medicinal preparations.

Medicinal topical compositions in accordance with the present invention comprise, as a rule, one or more medicaments in active concentration. For the sake of simplicity, reference is made to the legal provisions of the Federal Republic of Germany to differentiate neatly between cosmetic and medicinal use and corresponding products (for example Kosmetikverordnung [cosmetics regulation], Lebensmittelgesetz [food act] and Arzneimittelgesetz [pharmaceuticals act]).

It is also advantageous to add the active ingredient used in accordance with the invention to preparations which already comprise other active ingredients for other purposes, as additive.

Accordingly, cosmetic or topical dermatological compositions in accordance with the present invention may be used, for example, as a protective skin cream, cleansing milk, sun protection lotion, nutrient cream, day cream or night cream and the like, depending on their composition. If appropriate, it is possible and advantageous to use the compositions according to the invention as basis for pharmaceutical formulations.

If appropriate, other advantageous cosmetic and dermatological preparations are those which are present in the form of a sun protection product. These preferably comprise, in addition to the active ingredient used in accordance with the invention, at least one additional UVA filter and/or at least one UVB filter and/or at least one inorganic pigment.

However, also advantageous in accordance with the present invention is to create cosmetic and dermatological preparations whose main purpose is not the protection from sunlight, but which nevertheless comprise substances which protect from UV. For example, UV-A and/or UV-B filters are usually incorporated into day creams.

Preparations according to the invention may advantageously comprise substances which absorb UV radiation in the UVB range, the total amount of filters being, for example, 0.1% by weight to 30% by weight, preferably 0.5 to 10% by weight, in particular 1 to 6% by weight, based on the total weight of the preparations.

The UVB filters may be soluble in oil or in water. Examples of substances which are soluble in oil are, for example:

3-benzylidenecamphor and its derivatives, for example 3-(4-methylbenzylidene)camphor, 4-aminobenzoic acid derivatives, preferably 2-ethylhexyl 4-dimethylaminobenzoate, amyl 4-dimethylaminobenzoate;

cinnamic esters, preferably 2-ethylhexyl 4-methoxycinnamate, isopentyl 4-methoxycinnamate;

salicylic esters, preferably 2-ethylhexyl salicylate, 4-isopropylbenzyl salicylate, homomenthyl salicylate;

benzophenone derivatives, preferably 2-hydroxy-4-methoxybenzophenone, 2-hydroxy-4-methoxy-4'-methylbenzophenone, 2,2'-dihydroxy-4-methoxybenzophenone;

benzalmalonic esters, preferably di(2-ethylhexyl) 4-methoxybenzalmalonate;

2,4,6-trianilino-(p-carbo-2'-ethyl-1'-hexyloxy)-1,3,5-triazine

Advantageous substances which are soluble in water are:

2-phenylbenzimidazole-5-sulphonic acid and its salts, for example sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor such as, for example, 4-2-oxo-3-bomylidenemethyl) benzenesulphonic acid, 2-methyl5-(2-oxo-3-bomylidenemethyl)sulphonic acid and their salts.

Naturally, the list of the abovementioned UVB filters which may be used according to the invention is not intended to be limiting.

The invention also relates to the combination of a UVA filter according to the invention with a UVB filter, and/or a cosmetic or dermatological preparation according to the invention which also comprises a UVB filter.

It may also be advantageous to employ, in preparations according to the invention, UVA filters which cosmetic and/or dermatological preparations usually comprise. Such filters are preferably dibenzoylmethane derivatives, in particular 1-( 4'-tert-butylphenyl)-3-4'-methoxyphenyl) propane-1,3-dione and 1-phenyl-3-(4'-isopropylphenyl) propane-1,3-dione. The invention also relates to preparations which comprise these combinations. The same amounts of UVA filters which have been mentioned for UVB filters may be used.

Cosmetic and/or dermatological preparations in accordance with the present invention may also comprise inorganic pigments which are usually used in cosmetology for protecting the skin from UV rays. They are oxides of titanium, zinc, iron, zirconium, silicon, manganese, aluminium, cerium and mixtures of these, and modifications where the oxides are the active agents. Especially preferably, they are pigments based on titanium dioxide. The amounts mentioned for the above combinations may be used.

The cosmetic and dermatological preparations according to the invention may comprise cosmetically active ingredients, cosmetic auxiliaries and/or cosmetic additives conventionally used in such preparations, for example antioxidants, preservatives, bactericides, fragrances, antifoams, colorants, colour pigments, thickeners, surfactants, emulsifiers, plasticizers, moisturizers and/or humectants, fats, oils, waxes or other customary constituents of a cosmetic or dermatological formulation such as alcohols, polyols, polymers, foam stabilizers, electrolytes, organic solvents or silicone derivatives.

It is also advantageous to add customary antioxidants to the preparations in accordance with the present invention. Advantageous antioxidants which may be used in accordance with the invention are all those antioxidants which are suitable or conventional for cosmetic and/or dermatological applications.

The antioxidants are advantageously selected from the group consisting of amino acids (for example glycine, histidine, tyrosine, tryptophan) and their derivatives, imidazoles (for example urocaninic acid) and their derivatives, peptides such as D,L-carnosine, D-carnosine, L-carnosine and their derivatives (for example anserine), carotenoids, carotenes (for example α-carotene, β-carotene, lycopine) and their derivatives, liponic acid and its derivatives (for example dihydroliponic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (for example buthionine sulphoximines, homocysteine sulphoximine, buthionine sulphones, penta-, hexa-, heptathionine sulphoximine) at very low tolerated doses (for example pmol to μmol/kg), furthermore (metal)chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and their derivatives, unsaturated fatty acids and their derivatives (for example γ-linolenic acid, linolic acid, oleic acid), folic acid and its derivatives, alaninediacetic acid, flavonoids, polyphenols, catechols, ubiquinone and ubiquinol and their derivatives, vitamin C and derivatives (for example ascorbyl palmitate, Mg-ascorbyl phosphate, ascorbyl acetate), tocopherols and derivatives (for example vitamin E acetate), and coniferyl benzoate of benzoin resin, rutinic acid and its derivatives, ferulic acid and its derivatives, butylhydroxytoluene, butylhydroxyanisole, nordihydroguaiacic acid, nordihydroguaiaretic acid, trihydroxybutyrophenone, uric acid and its derivatives, mannose and its derivatives, zinc and its derivatives (for example ZnO, $ZnSO_4$) selenium and its derivatives (for example selenium methionine), stilbene and its derivatives (for example stilbene oxide, trans-stilbene oxide) and those derivatives of the abovementioned active ingredients which are suitable according to the invention (salts, esters, ethers, sugars, nucleotides, nucleosides, peptides and lipids).

The amount of antioxidants (one or more compounds) in the preparations is preferably 0.001 to 30% by weight, especially preferably 0.05–20% by weight, in particular 1–10% by weight, based on the total weight of the preparation.

If the antioxidant(s) is/are vitamin E and/or its derivatives, it is advantageous to choose the respective concentrations from the range 0.001–10% by weight, based on the total weight of the formulation.

If the cosmetic or dermatological preparation according to the present invention represents a solution or emulsion or dispersion, the following may be used as solvents:

water or aqueous solutions;

oils such as triglycerides of capric or caprylic acid, preferably castor oil;

fats, waxes and other natural and synthetic lipids, preferably esters of fatty acids with alcohols of low C number, for example with isopropanol, propylene glycol or glycerol, or esters of fatty alcohols with alkanolic acids of low C number or with fatty acids;

alcohols, diols or polyols of low C number and their ethers, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether, and analogous products.

In particular, mixtures of the abovementioned solvents are used. In the case of alcoholic solvents, water may be a further constituent.

The oil phase of the emulsions, oleogels or hydro- or lipodispersions in accordance with the present invention is advantageously selected from the group of the esters of saturated and/or unsaturated, branched and/or unbranched alkanecarboxylic acids with a chain length of 3 to 30 C atoms and saturated and/or unsaturated branched and/or unbranched alcohols with a chain length of 3 to 30 C atoms, from the group of the esters of aromatic carboxylic acids and saturated and/or unsaturated, branched and/or unbranched alcohols with a chain length of 3 to 30 C atoms. In this case, such ester oils may be selected advantageously from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, for example jojoba oil.

Furthermore, the oil phase may advantageously be selected from the group of the branched and unbranched hydrocarbons and hydrocarbon waxes, the silicone oils, the dialkyl ethers, the group of the saturated or unsaturated branched or unbranched alcohols and of the fatty acid triglycerides, viz. the triglycerol esters of saturated and/or unsaturated, branched and/or unbranched alkanecarboxylic acids with a chain length of 8 to 24, in particular 12–18, C atoms. For example, the fatty acid triglycerides may advantageously be selected from the group of the synthetic, semisynthetic and natural oils, for example olive oil, sunflower oil, soya oil, peanut oil, rapeseed oil, almond oil, palm oil, coconut oil, palm kernel oil and the like.

Any mixtures of such oil and wax components may also advantageously be employed in accordance with the present invention. If appropriate, it may also be advantageous to employ waxes, for example cetyl palmiate, as the only lipid component of the oil phase.

The oil phase is advantageously selected from the group consisting of 2-ethylhexyl isostearate, octyidodecanol, isotridecyl isononanoate, isoeicosan, 2-ethylhexyl cocoate, $C_{12-15}$-alkyl benzoate, caprylicicapric acid triglyceride, dicaprylyl ether.

Especially advantageous mixtures are those of $C_{12-15}$-alkyl benzoate and 2-ethylhexyl isostearate, those of $C_{12-15}$-alkyl benzoate and isotridecyl isononanoate and those of $C_{12-15}$-alkyl benzoate, 2-ethylhexyl isostearate and isotridecyl isononanoate.

Amongst the hydrocarbons, liquid paraffin, squalane and squalene may advantageously be used according to the present invention.

The oil phase may furthermore advantageously comprise cyclic or linear silicone oils, or consist entirely of such oils, but it is preferred to use an additional content of another oil phase components, apart from the silicone oil(s).

Cyclomethicone (octamethylcyclotetrasiloxane) is advantageously employed as silicone oil to be used according to the invention. However, other silicone oils may also be used advantageously in accordance with the present invention, for example hexamethylcyclotrisiloxane, polydimethylsiloxane, poly(methylphenylsiloxane).

Especially advantageous mixtures are furthermore those of cyclomethicone and isotridecyl isononanoate and of cyclomethicone and 2-ethylhexyl isostearate.

If appropriate, the aqueous phase of the preparations according to the invention advantageously comprises alcohols, diols or polyols of low C number, and their ethers, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether and analogous products, furthermore alcohols of low C number, for example ethanol, isopropanol, 1,2-propanediol, glycerol, and, in particular, one or more thickeners which may advantageously be selected from the group consisting of silicon dioxide, aluminium silicates, polysaccharides and their derivatives, for example hyaluronic acid, xanthan gum, hydroxypropylmethylcellulose, especially advantageously from the group of the polyacrylates, preferably a polyacrylate from the group of the so-called Carbopols, for example type 980, 981, 1382, 2984 and 5984 Carbopols, in each case singly or in combination.

Gels used according to the invention usually comprise alcohols of low C number, for example ethanol, isopropanol, 1,2-propanediol, glycerol and water, or an abovementioned oil in the presence of a thickener, which is preferably silicon dioxide or an aluminium silicate in the case of oily-alcoholic gels and preferably a polyacrylate in the case of aqueous-alcoholic or alcoholic gels.

Solid sticks comprise, for example, natural or synthetic waxes, fatty alcohols or fatty acid esters.

Customary basic materials which are suitable for use as cosmetic sticks in accordance with the present invention are liquid oils (for example liquid paraffin, castor oil, isopropyl myristate), semi-solid constituents (for example petrolatum, lanolin), solid constituents (for example beeswax, ceresine and microcrystalline waxes, or ozocerite) and waxes of high melting point (for example carnauba wax, candelilla wax).

Suitable propellants for cosmetic and/or dermatological preparations in accordance with the present invention which can be sprayed from aerosol containers are the customary known volatile, liquefied propellants, for example hydrocarbons (propane, butane, isobutane), which may be employed singly or as a mixture with each other. Pressurized air may also be used advantageously.

The person skilled in the art will, of course, be familiar with the fact that there are non-toxic propellants, which would be suitable in principle for putting into practice the present invention in the form of aerosol preparations; however, it is recommended to manage without these—in particular fluorohydrocarbons and fluorochbrohydrocarbons (FCHCs)—due to their unacceptable effect on the environment or other accompanying circumstances.

Cosmetic preparations in accordance with the present invention may also be present as gels which comprise not only an effective amount of active ingredient according to the invention and conventionally used solvents therefor, preferably water, but also organic thickeners, for example gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, go for example aluminium silicates such as, for example, bentonies, or a mixture of polyethylene glycol and polyethylene glycol stearate or polyethylene glycol distearate. The gel comprises the thickener for example in an amount of between 0.1 and 30% by weight, preferably between 0.5 and 15% by weight.

The examples which follow are intended to illustrate the present invention.

PREPARATION EXAMPLE 1

Synthesis in a Reaction Vessel (Suitable for Larger Batches)

In a reaction vessel, 0.5 g of Rink amide resin (0.2 mmol/g) are washed thoroughly with DMF and then treated with 5 ml of 20% (v/v) piperidine/DMF solution. After 3 minutes, the batch is filtered and is treated for a further 5 minutes with 5 ml of 20% piperidine/DMF. After thorough washing with DMF (approx. 50 ml), the resin is treated with 155.0 mg of Fmoc-Phe-OH and 128.1 mg of TBTU in 2 ml of DMF. After addition of 1.25 ml of 0.7 M N-methylmorpholine solution, the mixture is shaken for 30 minutes. After washing of the resin, completeness of the reaction is checked by a Kaiser test.

After the Fmoc protective group has been eliminated using 20% piperidine/DMF, 165.6 mg of Fmoc-Asp(OBut)-OH (0.4 mmol), 141.4 mg (0.4 mmol) of Fmoc-Leu-OH, 153.4 mg Fmoc-Ser(But)-OH and a further 238.7 mg (0.4 mmol) of Fmoc-Asn(Trt)-QH are coupled as described in the scheme above. Each time, the coupling efficiency is checked with the aid of the Kaiser test. After deblocking of the Fmoc protective group, the resin is washed thoroughly with DMF and finally dried. The protective group and the peptide are cleaved from the resin by 2 ml of trifluoroacetic acidithioanisole/pheno/water 90:5:3:2 (v,v). After the mixture has reacted for 2 hours, it is filtered and the fiftrate is directly added dropwise to 30 ml of iceoled diethyl ether. After centrifugation, the precipitate is washed thoroughly with diethyl ether and recentrifuged. The procedure is repeated three times. After dissolving the pellet in tert.-butanol/water (4:1, v/v), the solution is lyophilized.

The colourless lyophilisate is taken up in 5 ml of deionized water and again freeze-dried.

PREPARATION EXAMPLE 2

Synthesis of H-VVRP-NH$_2$ (Synthesis in Synthesizer)

A high-pressure glass column of the MilliGen 9050 peptide synthesizer is packed with 0.5 g of Rink amide resin (0.2 mmol/g) to which 2.5 g of glass beads (0.150–212 $\mu$m, Sigma) had been admixed. The N-terminal Fmoc protective group is then removed by adding 14.8 ml of 20% (v/v) piperidine/dimethylformamide (flow rate 7.4 ml/min). After washing with dimethylformamide (5 min at 7.4 ml/min), 108.3 mg (0.4 mmol) of Fmoc-proline and 128 mg of TBTU (0.4 mmol) in 1.25 ml of 0.7 M N-methylmorpholine solution are dissolved in DMF. After 3 minutes, this preactivated solution is pumped onto the column by the recycling method and coupled for 20 minutes. After washing with DMF, the N$^a$-Fmoc group is again eliminated by adding 20% piperidine in DMF. 259.5 mg of Fmoc-Arg(Pbf)-OH (0.4 mmol) are coupled as above as the next amino acid derivative. After coupling Fmoc-Val-OH and a further Fmoc-Val-OH (in each case 135.8 mg, 0.4 mmol), the Fmoc group is again eliminated, and the resin is washed thoroughly with DMF, removed from the column and dried thoroughly. The protective group and the peptide are cleaved from the resin by 2 ml of trifluoroacetic acid/thioanisole/phenol/water 90:5:3:2 (v/v). After the mixture has reacted for 2 hours, it is filtered and the filtrate is directly added dropwise to 30 ml of ice-cooled diethyl ether. After centrifugation, the precipitate is washed thoroughly with diethyl ether and recentrifuged. The procedure is repeated three times. After dissolving the pellet in tert.-butanol/water (4:1, v/v), the solution is lyophilized. The colourless lyophilisate is again taken up in 5 ml of deionized water and again freeze-dried.

Abbreviations

Fmoc: 9-fluorenylmethoxycarbonyl residue

Rink amide resin: 4-(2',4'-dimethylphenyl-Fmoc-aminomethyl)phenoxy resin

Fmoc-Arg(Pbf)-OH: $N^\alpha$-Fmoc-$N^G$-2,2,4,6,7-pentamethyidihydrobenzofuran-5-sulphonyl-arginine TBTU: 2-(1H-benzotriazol-1-yl)-1,1,3,3-tetramethyluronium tetrafluoroborate DMF dimethylformamide

EXAMPLE 1
W/O Cream

|  | % by weight |
|---|---|
| Liquid paraffin (DAB 9) | 10.00 |
| Petrolatum | 4.00 |
| Wool wax alcohol | 1.00 |
| PEG-7-hydrogenated castor oil | 3.00 |
| Aluminium stearate | 0.40 |
| Acetyl-NSLDF-NH$_2$ | 0.01 |
| Glycerol | 2.00 |
| Preservatives, colours, fragrance | q.s. |
| Water to | 100.00 |

EXAMPLE 2
W/O Lotion

|  | % by weight |
|---|---|
| Liquid paraffin (DAB 9) | 20.00 |
| Petrolatum | 4.00 |
| Glucose sesquiisostearate | 2.00 |
| Aluminium stearate | 0.40 |
| Acetyl-NSLDF-NH$_2$ | 0.005 |
| α-Tocopheryl acetate | 1.00 |
| Glycerol | 5.00 |
| Preservatives, colours, fragrance | q.s. |
| Water to | 100.00 |

EXAMPLE 3
O/W Lotion

|  | % by weight |
|---|---|
| Liquid paraffin (DAB 9) | 8.00 |
| Isopropyl palmitate | 3.00 |
| Petrolatum | 4.00 |
| Cetylstearyl alcohol | 2.00 |
| PEG 40 castor oil | 0.50 |
| Sodium cetyl stearyl sulphate | 0.50 |
| Sodium carbomer | 0.40 |
| H-NSLDF-NH$_2$ | 0.001 |
| Glycerol | 3.00 |
| α-Tocopherol | 0.20 |
| Octyl methoxycinnamate | 5.00 |
| Butylmethoxydibenzoylmethane | 1.00 |
| Preservatives, colours, fragrance | q.s. |
| Water to | 100.00 |

EXAMPLE 4
O/W Cream

|  | % by weight |
|---|---|
| Liquid paraffin (DAB 9) | 7.00 |
| Avocado oil | 4.00 |
| Glyceryl monostearate | 2.00 |
| Acetyl-NSLDF-NH$_2$ | 0.01 |
| Titanium dioxide | 1.00 |
| Sodium lactate | 3.00 |
| Glycerol | 3.00 |
| Preservatives, colours, fragrance | q.s. |
| Water to | 100.00 |

EXAMPLE 5
Liposome-containing Gel

|  | % by weight |
|---|---|
| Lecithin | 6.00 |
| Shea butter | 3.00 |
| H-NSLDF-NH$_2$ | 0.005 |
| α-Tocopherol | 0.20 |
| Biotin | 0.08 |
| Sodium citrate | 0.50 |
| Glycine | 0.20 |
| Urea | 0.20 |
| Sodium PCA | 0.50 |
| Hydrolysed collagen | 2.00 |
| Xanthan gum | 1.40 |
| Sorbitol | 3.00 |
| Preservatives, colours, fragrance | q.s. |
| Water to | 100.00 |

EXAMPLE 6
Gel

|  | % by weight |
|---|---|
| Carbopol 934 P | 2.00 |
| Triethanolamin | 3.00 |
| Acetyl-NSLDF-NH$_2$ | 0.001 |
| α-Tocopheryl acetate | 0.20 |
| Polyoxyethylene sorbitan fatty acid ester (Tween 20) | 0.50 |
| Glycerol | 2.00 |
| Sodium PCA | 0.50 |
| Hydrolysed collagen | 2.00 |
| Preservatives, colours, fragrance | q.s. |
| Water to | 100.00 |

EXAMPLE 7
Sun Protection Emulsion

|  | % by weight |
|---|---|
| Cyclomethicone | 2.00 |
| Cetyldimethicone copolyol | 0.20 |
| PEG 22-Dodecyl copolymer | 3.00 |
| Liquid paraffin (DAB 9) | 2.00 |
| Caprylic/capric acid triglyceride | 5.80 |
| Octyl methoxycinnamate | 5.80 |
| Butylmethoxydibenzoylmethane | 4.00 |

-continued

|  | % by weight |
|---|---|
| Acetyl-NSLDF | 0.001 |
| α-Tocopheryl acetate | 0.50 |
| ZnSO$_4$ | 0.70 |
| Na$_4$EDTA | 0.30 |
| Preservatives, colours, fragrance | q.s. |
| Water to | 100.00 |

EXAMPLE 8

Sun Protection Emulsion

|  | % by weight |
|---|---|
| Cyclomethicone | 2.00 |
| Cetylstearyl alcohol + PEG 40 hydrogenated castor oil + sodium cetyl stearyl sulphate | 2.50 |
| Glyceryl lanolate | 1.00 |
| Caprylic/capric acid triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.50 |
| H-NSLDF-NH$_2$ | 0.001 |
| α-Tocopheryl acetate | 1.00 |
| Na$_3$HEDTA | 1.50 |
| Preservatives, colours, fragrance | q.s. |
| Water to | 100.00 |

EXAMPLE 9

Sun Protection Emulsion

|  | % by weight |
|---|---|
| Cyclomethicone | 2.00 |
| Cetylstearyl alcohol + PEG 40 hydrogenated castor oil + sodium cetyl stearyl sulphate | 2.50 |
| Glyceryl lanolate | 1.00 |
| Caprylic/capric acid triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.75 |
| Acetyl-NSLDF-NH$_2$ | 0.001 |
| Na$_3$HEDTA | 1.50 |

-continued

|  | % by weight |
|---|---|
| Preservatives, colours, fragrance | q.s. |
| Water to | 100.00 |

EXAMPLE 10

Massage Cream

|  | % by weight |
|---|---|
| Stearyl alcohol | 2.00 |
| Petrolatum | 4.00 |
| Dimethicone | 2.00 |
| Isopropyl palmitate | 6.00 |
| Cetyl stearyl alcohol | 4.00 |
| PEG 40 hydrogenated castor oil | 2.00 |
| α-Tocopherol | 0.50 |
| H-NSLDF-NH$_2$ | 0.005 |
| Glycerol | 3.00 |
| Preservatives, colours, fragrance | q.s. |
| Water to | 100.00 |

EXAMPLE 11

Hair Tonic

|  | % by weight |
|---|---|
| Ethanol | 40.00 |
| Diisopropyl adipate | 0.10 |
| PEG 40 hydrogenated castor oil | 0.20 |
| H-NSLDF-NH$_2$ | 0.001 |
| α-Tocopheryl acetate | 0.10 |
| Preservatives, colours, fragrance | q.s. |
| Water to | 100.00 |

EXAMPLE 12

Spray Formulation

|  | % by weight |
|---|---|
| α-Tocopherol | 0.10 |
| Acetyl-NSLDF-NH$_2$ | 0.001 |
| Ethanol | 28.20 |
| Preservatives, colours, fragrance | q.s. |
| Propane/butane 25/75 | 100.00 |

What is claimed is:

1. A cosmetic or pharmaceutical preparation comprising a cosmetic or pharmaceutically effective amount of an oligopeptide or a homodimer, homotrimer or homotetramer thereof, wherein said oligopeptide is selected from the group consisting of Asn-Ser-Leu-Asp-Phe (SEQ ID NO: 1), Asn-Ser-Leu-Asp-Phe-Ser (SEQ ID NO: 2), Met-Asn-Ser-Leu-Asp-Phe (SEQ ID NO: 3), Met-Asn-Ser-Leu-Asp-Phe-Ser (SEQ ID NO: 4), Met-Asn-Ser-Leu-Asp-Phe-Ser-Ser (SEQ ID NO: 5), Ser-Met-Asn-Ser-Leu-Asp-Phe (SEQ ID NO: 6), Ser-Met-Asn-Ser-Leu-Asp-Phe-Ser (SEQ ID NO: 7) and Ser-Met-Asn-Leu-Asp-Phe-Ser-Ser (SEQ ID NO: 8).

2. The cosmetic or pharmaceutical preparation according to claim 1, wherein said oligopeptide or homodimer, homotrimer or homotetramer thereof is present in said preparation in a concentration of about 0.000001% to 10% by weight based on the total weight of the preparation.

3. The cosmetic or pharmaceutical preparation according to claim 1, wherein said oligopeptide or homodimer, homotrimer or homotetramer thereof is present in said preparation in a concentration of about 0.0001% to 1% by weight based on the total weight of the preparation.

4. The cosmetic or pharmaceutical preparation according to claim 1, wherein said oligopeptide or homodimer, homotrimer or homotetramer thereof is present in said preparation in a concentration of about 0.0001% to 0.1% by weight based on the total weight of the preparation.

5. A cosmetic or pharmaceutical preparation comprising a cosmetic or pharmaceutically effective amount of an oligopeptide or a homodimer, homotrimer or homotetramer thereof, wherein said oligopeptide is selected from the group consisting of Asn-Ser-Leu-Asp-Phe (SEQ ID NO: 1), Asn-Ser-Leu-Asp-Phe-Ser (SEQ ID NO: 2), Met-Asn-Ser-Leu-Asp-Phe (SEQ ID NO: 3), Met-Asn-Ser-Leu-Asp-Phe-Ser (SEQ ID NO: 4), Met-Asn-Ser-Leu-Asp-Phe-Ser-Ser (SEQ ID NO: 5), Ser-Met-Asn-Ser-Leu-Asp-Phe (SEQ ID NO: 6), Ser-Met-Asn-Ser-Leu-Asp-Phe-Ser (SEQ ID NO: 7) and Ser-Met-Asn-Leu-Asp-Phe-Ser-Ser (SEQ ID NO: 8), each of whose N-terminus is acylated by at least one unbranched alkanoyl group.

6. The cosmetic or pharmaceutical preparation according to claim 5, wherein said oligopeptide or homodimer, homotrimer or homotetramer thereof is present in said preparation in a concentration of about 0.000001% to 10% by weight based on the total weight of the preparation.

7. The cosmetic or pharmaceutical preparation according to claim 5, wherein said oligopeptide or homodimer, homotrimer or homotetramer thereof is present in said preparation in a concentration of about 0.0001% to 1% by weight based on the total weight of the preparation.

8. The cosmetic or pharmaceutical preparation according to claim 5, wherein said oligopeptide or homodimer, homotrimer or homotetramer thereof is present in said preparation in a concentration of about 0.0001% to 0.1% by weight based on the total weight of the preparation.

9. A method of preventing undesired skin pigmentation, said method comprising applying to skin an effective amount therefor of a cosmetic or pharmaceutical preparation according to any one of claims 1–8.

* * * * *